United States Patent [19]

Holzner

[11] Patent Number: 4,798,288

[45] Date of Patent: Jan. 17, 1989

[54] PLASTIC PACKING HAVING MULTIPLE COMPARTMENTS FOR SOLID AND LIQUID PRODUCTS

[75] Inventor: Günter Holzner, Carouge, Switzerland

[73] Assignee: Firmich SA, Geneva, Switzerland

[21] Appl. No.: 432,917

[22] PCT Filed: Jan. 14, 1982

[86] PCT No.: PCT/CH82/00005

§ 371 Date: Sep. 28, 1982

§ 102(e) Date: Sep. 28, 1982

[87] PCT Pub. No.: WO82/02700

PCT Pub. Date: Aug. 19, 1982

[30] Foreign Application Priority Data

Feb. 5, 1981 [CH] Switzerland ............................ 758/81

[51] Int. Cl.[4] .............................................. B65D 25/08
[52] U.S. Cl. ................................... 206/222; 206/219; 206/632
[58] Field of Search ............... 206/219, 221, 484, 461, 206/813, 632; 229/56

[56] References Cited

U.S. PATENT DOCUMENTS

| | | | |
|---|---|---|---|
| 2,932,385 | 4/1960 | Bollmeier et al. | 206/219 |
| 3,074,544 | 1/1963 | Bollmeier et al. | 206/219 |
| 3,478,952 | 11/1969 | Perlman | 206/521 |
| 3,578,239 | 5/1971 | Perlman | 383/107 |
| 3,608,709 | 9/1971 | Pike | 206/219 |
| 3,720,305 | 3/1973 | Barton | 206/219 |
| 3,809,224 | 5/1974 | Greenwood | 206/219 |
| 3,847,279 | 11/1974 | Montgomery | 206/219 |
| 3,915,302 | 10/1975 | Farrelly et al. | 206/813 |
| 3,983,994 | 10/1976 | Wysiotsky | 206/219 |
| 4,000,996 | 1/1977 | Jordan | 206/219 |
| 4,057,047 | 11/1977 | Gossett | 206/219 |
| 4,058,632 | 11/1977 | Evans et al. | 206/484 |
| 4,106,478 | 8/1978 | Higashijima | 206/219 |
| 4,280,621 | 7/1981 | Tonrey | 206/813 |
| 4,402,402 | 9/1983 | Pike | 206/219 |

FOREIGN PATENT DOCUMENTS 642360 6/1962 Canada ................................ 206/632

Primary Examiner—David T. Fidei
Attorney, Agent, or Firm—Pennie & Edmonds

[57] ABSTRACT

The invention relates to a plastic packing having multiple compartments for liquid and solid products having a joint common to both compartments constituted by at least two sheets of polymer material, one of which ruptures internally along a longitudinal axis, without the external walls of the packing rupturing, when an external pressure is applied to one of the compartments.

The packing of the invention enables the separate storage, in different compartments, of various incompatible substances, while enabling them to be mixed just before use, after rupture of the internal portion of the joint separating the said compartments.

The packing of the invention in particular enables the preparation of novel and advantageous devices designed for the deodorizing of enclosed spaces.

5 Claims, 2 Drawing Sheets

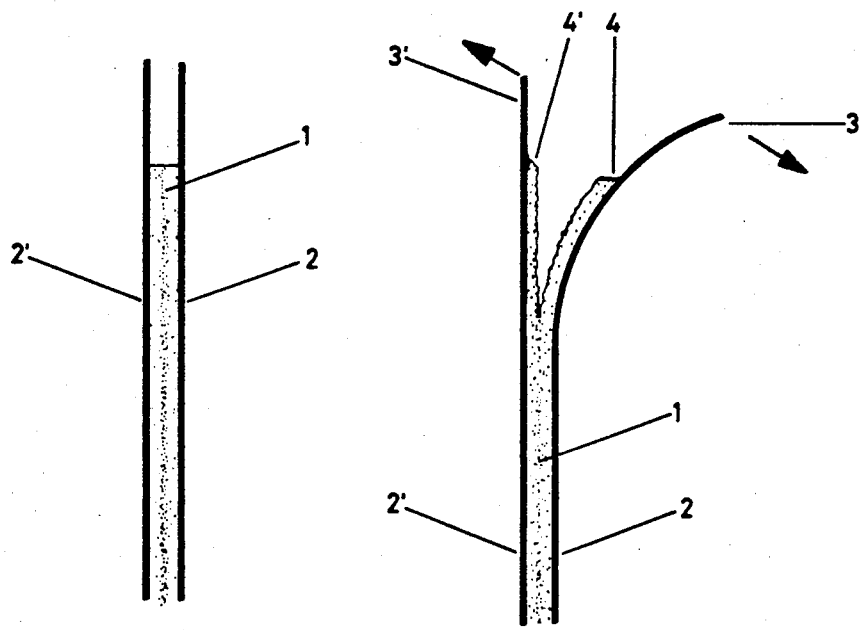
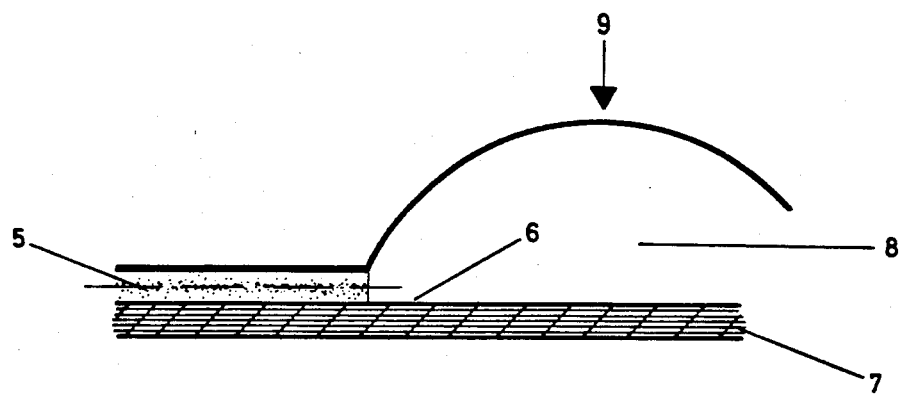

PLASTIC PACKING HAVING MULTIPLE COMPARTMENTS FOR SOLID AND LIQUID PRODUCTS

OBJECT OF THE INVENTION

One of the objects of the present invention relates to the industrial production of an inexpensive packing which is ready for use (unit dose) for pharmaceutical, insecticide cosmetic or other chemical products of various types, which packing is designed to contain at least two substances which cannot be left in contact for long periods and which must therefore be mixed just before use.

BACKGROUND OF THE INVENTION

Numerous pharmaceutical or chemical active substances are preferably used in the form of solutions or mixtures with other ingredients or excipients. However, in practice, many of these active substances are less stable in solution than in their solid state, or even incompatible with certain of the other ingredients or additives of the solution in question. This is due, in particular, to the fact that when these mixtures are heated, for example during a sterilization process, or kept for long periods, they give rise to chemical reactions which render their constituents completely inactive or at least substantially decrease their activity.

In the case of a number of clinical infusion solutions, it has proved advantageous to use combinations of glucose and amino acids of various types. The drawback, which is at present difficult to overcome, of these combinations lies in the incompatibility of the products when they are heated, and in particular in the case of sterilization. The aldehyde group of the glucose in effect reacts with the free amino groups of the amino acids such as lysine (Maillard reaction) leading to the formation of Schiff bases which are the cause, inter alia, of the dark colouring of these solutions. This type of reaction does not only lead to modification of the physical aspect of these solutions, but also has a detrimental effect on biological compatibility, thus making the solutions completely unsuitable for infusion.

One of the solutions proposed as a remedy for these drawbacks consists in replacing, in sterilizable mixtures for infusion, glucose by sorbitol, as this latter product does not have an aldehyde group. However, sorbitol has several drawbacks which limit its use from the legal point of view.

If use is made, on the other hand, of packings having multiple compartments in accordance with the invention, it is possible to sterilize and keep the glucose and amino acid solutions separately. The internal portion of the joint common to both compartments in question is broken, just before use, under the action of an external pressure, for example a finger pressure, and the two solutions may then be immediately contacted and mixed.

A device which has recently been developed for the perfuming of rooms comprises a sachet of specially adapted polymer material containing a perfuming solution (see, in this respect, the International Appl. WO 81/00051). The perfume vapours diffuse slowly through the wall of polymer material and may thus perfume the room for a long period. A problem arises, however, during the storage of these devices before sale. As a result of the diffusion of the perfume vapours through the walls of polymer material of the packing, a considerable reduction in the initial amount of active substances may be observed.

SUMMARY OF THE INVENTION

By using packings having multiple compartments of the invention, this drawback may be readily overcome. The perfuming solution is maintained in a compartment having walls which cannot be permeated by the perfume vapours and wherein one of the joints may be ruptured under the action of external pressure, then, when the walls of the joint have been broken, just before use, the solution passes into a compartment having walls of polymer material which may be permeated by the perfume vapours which may then be diffused in a uniform manner into the surrounding atmosphere.

The present invention relates to a plastic packing having multiple compartments for liquid and solid products, characterised in that it contains a joint which is common to both compartments constituted by at least two sheets of polymer material, one of which is ruptured internally along a longitudinal axis without the external walls of the said packing breaking when an external pressure is applied to one of the compartments.

The present invention also relates to a plastic packing having two compartments as defined above, characterised in that the said compartments have different volumes and in that the smaller compartment is housed within the larger compartment and in that the rupture of the smaller compartment is caused by an external pressure applied to the larger compartment.

The invention also relates to a plastic packing having multiple compartments as defined above, and designed to contain perfumes, insecticides or other active substances, characterised in that at least one of the walls of the said compartments comprises a sheet of polymer material enabling the external diffusion of the said perfumes, insecticides or other active substances.

In accordance with a particular embodiment of the invention, the sheet of polymer material which ruptures internally along a longitudinal axis under the action of an external pressure is constituted by a polymer material of the foam type.

Materials of this type include in particular polyethylene, polypropylene, polyamides, polyvinyl chloride and polyesters. These are preferably provided in the form of sheets having a thickness of between approximately 0.005 and 0.2 mm.

The invention relates lastly to a plastic packing having multiple compartments which may be sterilized by heating, as defined above.

DESCRIPTION OF THE DRAWINGS

FIG. 4 is an enlarged section of a tearable joint (composite sheet) separating two compartments in accordance with the invention, before rupture.

FIG. 5 is an enlarged section of this same joint when it is commencing its internal rupture.

FIG. 6 is an enlarged section of the tearable joint (13) separating the two compartments of the packing of the invention as shown in FIG. 2.

DESCRIPTION OF THE PREFERRED EMBODIMENTS

Figure 1:
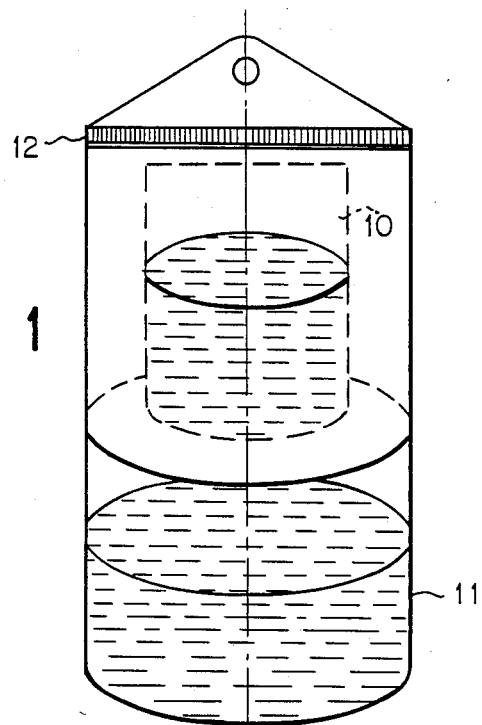
FIG. 1 is a view of a filled packing obtained in accordance with a particular embodiment of the invention and designed for the packing of solutions for infusion. It comprises in particular a tearable internal pocket (10) and an outer casing (11) sealed by heating by means of a solid joint (12).
Figure 2:
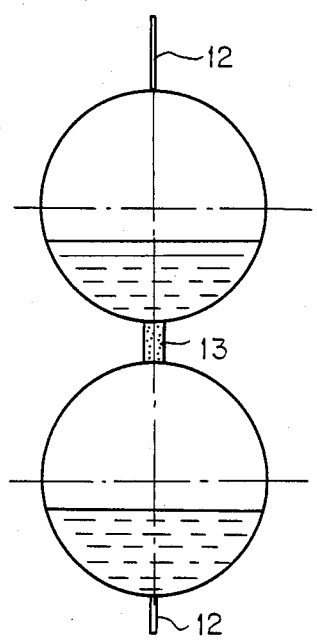
FIG. 2 is a cross-section through a packing having two compartments in accordance with the invention, each of the said compartments containing a liquid. In its upper and lower portions, it comprises a heat-sealed solid joint (12), the two compartments being separated by a tearable joint (13) in accordance with the invention.
Figure 3:
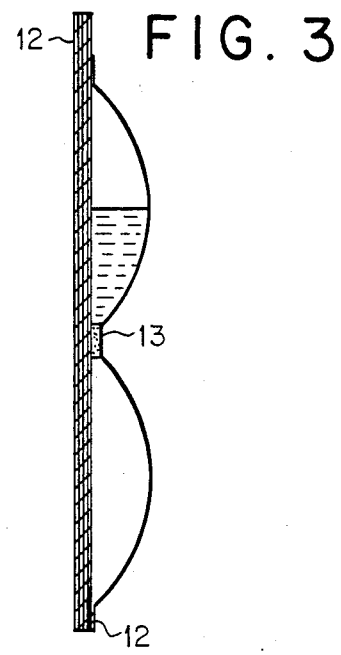
FIG. 3 is a longitudinal section through a packing having two compartments in accordance with the invention and containing in its upper portion a liquid such as a perfume, the lower compartment being empty. In its upper and lower portions, it comprises a solid heat-sealed joint (12), the two compartments being separated by a tearable joint (13) in accordance with the invention.

In accordance with a preferred embodiment of the invention, a plastic packing having multiple compartments designed for perfuming the surrounding atmosphere (rooms, wardrobes or cars for example) consists in a device in which one of the compartments is designed to act as a leak-tight recipient for the perfume solution, the other compartment being constituted by a polymer material which may be permeated by the perfume vapours. This latter compartment may, of course, be embodied in an aesthetically pleasing form, such as a fruit or flower for example. The leak-tight container is opened just before use by the pressure of a finger causing rupture of the ad hoc joint and the perfume solution penetrates into the compartment made of polymer material which may be permeated by perfume vapours which are then slowly diffused into the surrounding atmosphere.

At least one of the compartments of the plastic packing consists in the combination of an external leak-tight sheet (cover sheet) and a sheet of polymer material of the foam type coupled to the internal portion of the said cover sheet. This sheet of the foam type is relatively resistant to transverse traction but may, in contrast, be readily broken into two portions in a longitudinal plane. When a sheet (1) of this type is sealed or simply glued to two tear-resistant sheets (2) and (2') in order to form an assembly of the "sandwich" type (composite sheet: FIG. 4), it is then possible to separate the said resistant sheets by pulling their corresponding free ends (3) and (3'). The intermediate sheet (1) of the foam type then separates into two portions (4) and (4') which both adhere to each of the tear-resistant cover sheets (2) and (2') (FIG. 5).

In comparison with systems having a weakened rupture zone, such as for example those having a partial indentation of the plastic sheets, a thinner tear zone, an adhesive joint or a heat-sealed tearing seam, this device having separable layers has the advantage that it only makes the breaking force dependent on the internal resistance of the sheet of foam and not on the quality of the joint or the seam of the mechanically weakened area.

The internal resistance of the sheet of foam does not depend solely on the polymer material used but also, to a large extent, on the density of the said foam. Control of this latter factor therefore enables accurate monitoring of the rupture strength. This may in particular be maintained at a constant value during the mass production of these devices.

The thickness of the sheet of foam is preferably between 0.005 and 0.2 mm. This type of sheet may be commercially obtained (see in this respect the European Pat. No. 0 004 633).

As mentioned above, the sheet of foam may be obtained from polyethylene, polypropylene, polyamide, polyvinyl chloride, polyester, polystyrene or any other suitable polymer material.

The cover sheet is preferably constituted by polyamide, polyester, polyethylene, polypropylene or any other polymer material commonly used for the production of packing sheets.

The compartment to be opened by rupture is constituted by sheets of the foam type having two layers (sheet of foam itself+cover sheet). It is also possible to fix, by soldering or by means of an adhesive, the sheet of foam (5) to a so-called two layer sheet on the internal face (6) of the outer casing (7). An internal pocket (8) is thereby constituted and may be ruptured by the application of a slight external pressure (9) and one of whose walls consists of the said two layer sheet, the other being formed by that of the outer casing (FIG. 6).

I claim:

1. Plastic packing having multiple compartments for liquid and solid materials, characterized in that it comprises a joint common to both compartments constituted by at least two sheets of polymer material, one of which is polymer foam material and ruptures internally along a longitudinal axis without the external walls of the packing rupturing, when an external pressure is applied to one of the compartments.

2. Plastic packing having two compartments as claimed in claim 1, characterized in that the said compartments have different volumes and in that the smaller of the two is housed within the larger and in that the rupture of the smaller compartment is caused by an external pressure applied to the larger compartment.

3. Plastic packing having multiple compartments as claimed in claim 1, designed to contain perfumes, insecticides or other active substances, characterised in that at least one of the walls of the said compartments comprises a sheet of polymer material enabling the external diffusion of the said perfumes, insecticides or other active substances.

4. Plastic packing having multiple compartments as claimed in one of claims 1 to 3, characterized in that the sheet of polymer foam material is polyethylene, polypropylene, polyamide, polyvinylchloride, polyester or polyestyrene foam and has a thickness of between 0.005 and 0.2 mm.

5. Plastic packing having sterilisable multiple compartments as claimed in one of claims 2 to 3.

* * * * *